(12) United States Patent
Hashida et al.

(10) Patent No.: US 9,151,204 B2
(45) Date of Patent: Oct. 6, 2015

(54) DEVICE FOR DETECTING PARTICULATE MATTER IN EXHAUST GAS

(75) Inventors: Tatsuhiro Hashida, Susono (JP); Hiroki Nishijima, Suntou-gun (JP)

(73) Assignee: TOYOTA JIDOSHA KABUSHIKI KAISHA, Aichi-ken (JP)

( * ) Notice: Subject to any disclaimer, the term of this patent is extended or adjusted under 35 U.S.C. 154(b) by 656 days.

(21) Appl. No.: 13/509,894

(22) PCT Filed: Feb. 25, 2011

(86) PCT No.: PCT/JP2011/054359
§ 371 (c)(1),
(2), (4) Date: May 15, 2012

(87) PCT Pub. No.: WO2012/114518
PCT Pub. Date: Aug. 30, 2012

(65) Prior Publication Data
US 2012/0260636 A1  Oct. 18, 2012

(51) Int. Cl.
*F01N 3/00* (2006.01)
*F01N 11/00* (2006.01)
*F02D 41/14* (2006.01)
*F02D 41/22* (2006.01)
(Continued)

(52) U.S. Cl.
CPC ............ *F01N 11/00* (2013.01); *F02D 41/1466* (2013.01); *F02D 41/222* (2013.01); *G01N 35/00613* (2013.01); *F01N 2550/04* (2013.01); *F01N 2560/05* (2013.01); *F02D 41/1494* (2013.01); *G01N 15/0656* (2013.01); *G01N 35/00712* (2013.01); *Y02T 10/40* (2013.01); *Y02T 10/47* (2013.01)

(58) Field of Classification Search
CPC . F01N 11/00; F02D 41/1466; F02D 41/1494; G01N 35/00613; G01N 35/00712
USPC ..................................................... 60/276, 277
See application file for complete search history.

(56) References Cited

U.S. PATENT DOCUMENTS

2007/0125349 A1* 6/2007 Zanini-Fisher et al. ...... 123/679
2008/0307770 A1* 12/2008 Brahma et al. ................. 60/273
(Continued)

FOREIGN PATENT DOCUMENTS

DE  10 2007 047 081 A1  4/2009
DE  10 2009 049 669 A1  4/2011
(Continued)

*Primary Examiner* — Thomas Denion
*Assistant Examiner* — Jason Shanske
(74) *Attorney, Agent, or Firm* — Sughrue Mion, PLLC (57) ABSTRACT

Disclosed is an abnormality determination device capable of checking for abnormal particulate matter detection by a particulate matter detection sensor. The particulate matter detection sensor 10 includes a sensor element section 12, which comes into contact with particulate matter in exhaust gas in an exhaust pipe 6 of an internal combustion engine 2, and changes its output in accordance with the amount of particulate matter attached to the sensor element section 12. A heater for the particulate matter detection sensor 10 is capable of heating the sensor element section 12 to a particulate matter elimination temperature (T3) at which the particulate matter attached to the sensor element section 12 is eliminated from the sensor element section 12. An ECU 50 determines, in accordance with output changes (S1 to S4) occurring in the particulate matter detection sensor 10 during heater control, whether or not the particulate matter detection sensor 10 is abnormal.

13 Claims, 4 Drawing Sheets (51) Int. Cl.
*G01N 35/00* (2006.01)
*G01N 15/06* (2006.01)

(56) References Cited

U.S. PATENT DOCUMENTS

2009/0056416 A1* 3/2009 Nair et al. .................... 73/28.01
2010/0312488 A1 12/2010 Diehl et al.
2011/0088450 A1* 4/2011 Ante et al. ................... 73/23.33

2011/0109331 A1* 5/2011 Nelson et al. ................. 324/693

FOREIGN PATENT DOCUMENTS

| EP | 1 624 166 B1 | 7/2007 |
| JP | 2009-144512 A | 7/2009 |
| JP | 2010-275917 A | 12/2010 |
| JP | 2010-275977 A | 12/2010 |
| JP | 2011-017289 A | 1/2011 |

* cited by examiner

DEVICE FOR DETECTING PARTICULATE MATTER IN EXHAUST GAS

CROSS REFERENCE TO RELATED APPLICATIONS

This application is a National Stage of International Application No. PCT/JP2011/054359 filed Feb. 25, 2011, the contents of all of which are incorporated herein by reference in their entirety.

TECHNICAL FIELD

The present invention relates to an abnormality determination device for a particulate matter detection sensor (PM sensor) that detects particulate matter in exhaust gas.

BACKGROUND ART

For use in an exhaust emission control system having a DPF (Diesel Particulate Filter) and a PM sensor for detecting the amount of particulate matter (hereinafter may be referred to as the PM) in exhaust gas, a fault determination device for determining whether the PM sensor is faulty is conventionally known as disclosed, for instance, in JP-A-2010-275977. More specifically, a conventional technology applied to this fault determination device is used in a configuration in which the PM sensor is installed downstream of the DPF in an exhaust pipe, and determines, in accordance with a change in a PM sensor output prevailing after regeneration of the DPF, whether the PM sensor is faulty.

When the PM collection performance of the DPF is normal, the DPF can collect the PM in the exhaust gas. In other words, an extremely small amount of PM flows downstream of the DPF as far as the DPF's PM collection performance is normal. Even if an attempt is made to check whether the PM sensor generates a normal output in accordance with the arrival of the PM at the PM sensor, it is virtually difficult to perform such a check when an extremely small amount of PM flows downstream of the DPF.

As such being the case, the above conventional technology notes the fact that the PM collection performance is temporarily degraded during a certain period after the regeneration of the DPF, and determines whether the PM sensor is faulty by checking an output of the PM sensor during the period during which the PM collection performance is degraded. In other words, as a certain limit is imposed on the amount of PM collected by the DPF, it is necessary to recover the DPF's PM collection performance by regenerating the DPF as needed. According to the JP-A-2010-275977, the DPF's PM collection performance is temporarily degraded immediately after the above-mentioned DPF regeneration process is performed. While the PM collection performance is degraded, the amount of PM flowing downstream of the DPF is larger than while normal PM collection performance is exhibited. Whether or not the PM sensor is faulty can be determined by checking an output of the PM sensor during the period during which the PM collection performance is degraded.

PRIOR ART LITERATURE

Patent Documents

Patent Document 1: JP-A-2010-275977
Patent Document 2: JP-A-2009-144512

SUMMARY OF THE INVENTION

Technical Problem

Particulate matter detection sensors (PM sensors) based on various methods are used to detect the PM in the exhaust gas. For example, a capacitive PM sensor, which is used with the device described in JP-A-2010-275977, and an electrically resistive PM sensor, which is based on changes in electrical resistance, are employed to detect the PM in the exhaust gas. These PM sensors are capable of detecting the existence and amount of PM in the exhaust gas in accordance with a change in electrical physical quantity, which is based on the PM attached to a sensor element section.

In a configuration in which the PM sensor is installed downstream of the DPF as is the case with the above-described conventional technology, the output of the PM sensor can be used to detect an unintended increase in the concentration of PM flowing downstream of the DPF or a fault in the PM collection performance of the DPF. Further, in a configuration in which the PM sensor is installed upstream of the DPF, the output of the PM sensor can be used to accurately detect the amount of PM in the exhaust gas and have the results of detection reflected in operation control of an internal combustion engine.

When an output change exhibited by the PM sensor is brought about normally by PM, the results of detection based on the output change can be used properly. However, the inventors of the present invention have found, as a result of intensive studies, that PM sensor output changes are also brought about by various factors other than the PM. Output changes brought about by factors other than the PM are abnormal output changes and cannot be used as the basis of detecting the existence and amount of PM. The results of detection based on such abnormal output changes also cannot be used as the results of PM amount detection or the like. Failure to accurately distinguish between such abnormal PM sensor output changes and normal PM sensor output changes may decrease the PM detection accuracy of the PM sensor or cause erroneous PM detection.

The present invention has been made to solve the above problem. An object of the present invention is to provide an abnormality determination device that is capable of checking for abnormal particulate matter detection by a particulate matter detection sensor by distinguishing between the particulate matter detection sensor's normal output changes caused by PM and output changes caused by factors other than the PM.

Solution to Problem

To achieve the above-mentioned purpose, a first aspect of the present invention is an abnormality determination device for a particulate matter detection sensor that includes a sensor element section installed in an exhaust path of an internal combustion engine, output means for changing an output in accordance with the amount of PM attached to the sensor element section, and a heater capable of heating the sensor element section to a PM elimination temperature at which the PM attached to the sensor element section is eliminated from the sensor element section, the abnormality determination device comprising:

heater control means for controlling the heater to heat the sensor element section; and determination means for determining, in accordance with a change in the output of the particulate matter detection sensor that is brought about by the heater control means' control of the heater, whether the particulate matter detection sensor is abnormal.

A second aspect of the present invention is the abnormality determination device for the particulate matter detection sensor according to the first aspect, wherein the heater control means includes means for controlling the heater so as to heat the sensor element section after an output change equivalent to an increase in the amount of PM attached to the sensor element section is exhibited by the particulate matter detection sensor; and wherein the determination means includes means for determining, depending on whether an output change equivalent to a decrease in the amount of PM attached to the sensor element section is exhibited by the particulate matter detection sensor when the temperature of the sensor element section is lower than the PM elimination temperature in a situation where the heater is controlled to heat the sensor element section, whether the particulate matter detection sensor is abnormal.

A third aspect of the present invention is the abnormality determination device for the particulate matter detection sensor according to the first aspect or the second aspect, wherein the heater control means includes at least either specific-temperature heater control means for controlling the heater, for a predetermined period of time, to maintain the sensor element section at at least one predetermined temperature lower than the PM elimination temperature or specific-temperature-range heater control means for controlling the heater, for a predetermined period of time, to maintain the sensor element section within a predetermined temperature region having an upper-limit temperature lower than the PM elimination temperature.

A fourth aspect of the present invention is the abnormality determination device according to any one of the first to third aspects, wherein the specific-temperature heater control means includes stepwise heater control means for controlling the heater in such a manner that the sensor element section reaches the PM elimination temperature through gradual temperature changes brought about in at least two steps.

A fifth aspect of the present invention is the abnormality determination device for the particulate matter detection sensor according to the fourth aspect, wherein the stepwise heater control means provides at least either first control for controlling the heater, for a predetermined period of time, to maintain the sensor element section at a first temperature, which is not lower than a temperature at which water attached to the sensor element section is eliminated and is lower than a temperature at which fuel attached to the sensor element section is eliminated, or second control for controlling the heater, for a predetermined period of time, to maintain the sensor element section at a second temperature, which is not lower than a temperature at which fuel or organic matter attached to the sensor element section is eliminated and is lower than the PM elimination temperature.

A sixth aspect of the present invention is the abnormality determination device for the particulate matter detection sensor according to any one of the first to fifth aspects, wherein the heater control means includes means for controlling the heater to heat the sensor element section at a temperature rise rate appropriate for distinguishing between a first output change, which is an output change exhibited by the particulate matter detection sensor before the sensor element section reaches the PM elimination temperature, and a second output change, which is an output change exhibited by the particulate matter detection sensor upon PM elimination from the sensor element section when the sensor element section reaches the PM elimination temperature.

A seventh aspect of the present invention is the abnormality determination device for the particulate matter detection sensor according to any one of the first to sixth aspects, wherein the determination means includes means for determining, in accordance with an output change exhibited by the particulate matter detection sensor within a temperature region within which water attached to the sensor element section is eliminated as the heater control means controls the heater, whether the particulate matter detection sensor is abnormal.

An eighth aspect of the present invention is the abnormality determination device for the particulate matter detection sensor according to any one of the first to seventh aspects, wherein the determination means includes means for determining, in accordance with an output change exhibited by the particulate matter detection sensor within a temperature region within which fuel attached to the sensor element section is eliminated or a temperature region within which organic matter attached to the sensor element section is eliminated as the heater control means controls the heater, whether the particulate matter detection sensor is abnormal.

A ninth aspect of the present invention is the abnormality determination device for the particulate matter detection sensor according to any one of the first to eighth aspects, wherein the particulate matter detection sensor includes a holding part, which is connected to an exhaust pipe of the internal combustion engine and secures the sensor element section to the inside of the exhaust pipe, and a wiring section, which is disposed in the holding part and includes wiring for transmitting a signal of the sensor element section to the outside; and wherein the determination means includes condensation determination means for determining, in accordance with an output change exhibited by the particulate matter detection sensor within a temperature region within which water condensed on the wiring section is eliminated as the heater control means controls the heater, whether the particulate matter detection sensor is abnormal.

A tenth aspect of the present invention is the abnormality determination device for the particulate matter detection sensor according to the ninth aspect, wherein the heater control means includes means for controlling the temperature of the heater in such a manner that the sensor element section is maintained, for a predetermined period of time, at a predetermined temperature at which water condensed on the wiring section is eliminated or within a predetermined temperature range having a lower-limit temperature not lower than a temperature at which the water condensed on the wiring section is eliminated; and wherein the condensation determination means includes means for determining, in accordance with an output change exhibited by the particulate matter detection sensor within the predetermined period of time, whether the particulate matter detection sensor is abnormal.

An eleventh aspect of the present invention is the abnormality determination device for the particulate matter detection sensor according to any one of the first to tenth aspects, wherein the heater control means includes means for controlling the heater so as to heat the sensor element section to the PM elimination temperature; and wherein the determination means includes means for determining, in accordance with an output change exhibited by the particulate matter detection sensor when the sensor element section is heated to the PM elimination temperature, whether the particulate matter detection sensor is abnormal.

A twelfth aspect of the present invention is the abnormality determination device for the particulate matter detection sensor according to any one of the first to eleventh aspects, further comprising:

determination start means for causing the heater control means to control the heater and the determination means to check for an abnormality in the particulate matter detection sensor when the particulate matter detection sensor exhibits an output change sharper than indicated by a predetermined change rate.

A thirteenth aspect of the present invention is a fault determination device for a particulate matter collection system that includes a particulate filter installed in an exhaust path of an internal combustion engine and a particulate matter detection sensor having a sensor element section disposed downstream of the particulate filter in the exhaust path, an output section for changing an output in accordance with the amount of PM attached to the sensor element section, and a heater capable of heating the sensor element section to a PM elimination temperature at which the PM attached to the sensor element section is eliminated from the sensor element section, the fault determination device comprising:

the abnormality determination device according to any one of the first to twelfth aspects that checks for an abnormality in the particulate matter detection sensor after an output change indicative of a PM amount increase corresponding to a fault in the particulate filter is exhibited by the particulate matter detection sensor; and fault determination means for, when the abnormality determination device concludes that the particulate matter detection sensor is not abnormal, concluding that the particulate filter is faulty.

A fourteenth aspect of the present invention is a device for detecting particulate matter in exhaust gas, the device comprising:

a particulate matter detection sensor having a sensor element section installed in a distribution path for the exhaust gas whose PM content is to be detected, output means for generating an output that changes in accordance with the amount of PM attached to the sensor element section, and a heater capable of heating the sensor element section to a PM elimination temperature at which the PM attached to the sensor element section is eliminated from the sensor element section;

the abnormality determination device according to any one of the first to twelfth aspects, the abnormality determination device checking for an abnormality in the particulate matter detection sensor after an output change indicative of a PM amount increase is exhibited by the particulate matter detection sensor;

output determination means for determining, in accordance with an abnormality determination result about the particulate matter detection sensor that is produced by the abnormality determination device, whether or not the output change indicative of a PM amount increase in the particulate matter detection sensor is to be used for detecting the amount of PM in the exhaust gas; and PM amount detection means for detecting the amount of PM in the exhaust gas in accordance with the output change in the particulate matter detection sensor that the output determination means has decided to use for detecting the amount of PM in the exhaust gas.

Advantages of the Invention

If an output change exhibited by the particulate matter detection sensor is caused by the PM attached to the sensor element section, the PM attached to the sensor element section is removed at the PM elimination temperature by a heater heating the sensor element section, and this causes the particulate matter detection sensor to exhibit an output change in accordance with the elimination of the PM. If, on the contrary, an output change caused by the heater's heating operation is encountered at a temperature other than the PM elimination temperature or an expected output change does not occur when the attached PM is eliminated at the PM elimination temperature, it is conceivable that the output change exhibited by the particulate matter detection sensor is not caused by the PM attached to the sensor element section.

The first aspect of the present invention can determine, in accordance with an output change caused by the heater's heating operation, whether or not the particulate matter detection sensor is abnormal. When the output change caused by the heater's heating operation is taken into consideration, it is possible to distinguish between the particulate matter detection sensor's normal output changes caused by PM and output changes caused by factors other than the PM. This makes it possible to determine whether particulate matter detection is abnormal.

If the particulate matter detection sensor exhibits an output change equivalent to a decrease in the amount of attached PM at a temperature lower than the PM elimination temperature when a heating operation is performed by the heater after an output change equivalent to an increase in the amount of attached PM, it is conceivable that the output change equivalent to the increase in the amount of attached PM is caused by a factor other than the attached PM.

When the above is taken into consideration, the second aspect of the present invention can accurately distinguish between the particulate matter detection sensor's normal output changes caused by the PM and output changes caused by factors other than the PM.

When heating control is exercised over the heater, the third aspect of the present invention can certainly check for a change in the output of the particulate matter detection sensor at a temperature lower than the PM elimination temperature. This makes it possible to accurately distinguish between the particulate matter detection sensor's normal output changes caused by the PM and output changes caused by factors other than the PM.

When heating control is exercised over the heater, the fourth aspect of the present invention can certainly check for a change in the output of the particulate matter detection sensor at a temperature lower than the PM elimination temperature. This makes it possible to accurately distinguish between the particulate matter detection sensor's normal output changes caused by the PM and output changes caused by factors other than the PM.

When heating control is exercised over the heater, the fifth aspect of the present invention can determine whether an output change in the particulate matter detection sensor is caused by water attached to the sensor element section and/or fuel attached to the sensor element section. This makes it possible to accurately distinguish between the particulate matter detection sensor's normal output changes caused by the PM and output changes caused by factors other than the PM while identifying the causes of such output changes.

When heating control is exercised over the heater, the sixth aspect of the present invention can certainly check for a change in the output of the particulate matter detection sensor at a temperature lower than the PM elimination temperature. This makes it possible to accurately distinguish between the particulate matter detection sensor's normal output changes caused by the PM and output changes caused by factors other than the PM.

When heating control is exercised over the heater, the seventh aspect of the present invention can determine whether an output change in the particulate matter detection sensor is caused by water attached to the sensor element section. This makes it possible to accurately distinguish between the particulate matter detection sensor's normal output changes caused by the PM and output changes caused by factors other than the PM while identifying the causes of such output changes.

When heating control is exercised over the heater, the eighth aspect of the present invention can determine whether an output change in the particulate matter detection sensor is caused by fuel or organic matter attached to the sensor element section. This makes it possible to accurately distinguish between the particulate matter detection sensor's normal output changes caused by the PM and output changes caused by factors other than the PM while identifying the causes of such output changes.

When heating control is exercised over the heater, the ninth aspect of the present invention can determine whether an output change in the particulate matter detection sensor is caused by water condensed on the wiring section. This makes it possible to accurately distinguish between the particulate matter detection sensor's normal output changes caused by the PM and output changes caused by factors other than the PM while identifying the causes of such output changes.

The tenth aspect of the present invention can maintain the heater temperature for a predetermined period of time to determine with increased certainty whether an output change in the particulate matter detection sensor is caused by condensed water.

If the heater heats the sensor element section to the PM elimination temperature after an output change equivalent to an increase in the amount of attached PM is exhibited by the particulate matter detection sensor, the PM should be eliminated from the sensor element section so that the particulate matter detection sensor exhibits an output change equivalent to a decrease in the amount of attached PM. However, if, contrary to the above expectation, the particulate matter detection sensor does not exhibit such an output change, it is conceivable that the output change equivalent to an increase in the amount of attached PM is caused by a factor other than the attached PM.

When the above is taken into consideration, the eleventh aspect of the present invention can accurately distinguish between the particulate matter detection sensor's normal output changes caused by the PM and output changes caused by factors other than the PM.

When the particulate matter detection sensor exhibits a sudden output change, the twelfth aspect of the present invention can immediately start determining whether the output change is caused by an abnormality in the particulate matter detection sensor or caused by a sharp change in the amount of PM while the particulate matter detection sensor is normal. This makes it possible to immediately identify a sharp change in the amount of PM, which is to be dealt with.

The thirteenth aspect of the present invention can accurately determine whether the particulate matter collection system is faulty by distinguishing between the particulate matter detection sensor's normal output changes caused by the PM and output changes caused by factors other than the PM.

The fourteenth aspect of the present invention can inhibit an erroneous PM amount detection by determining whether a change in the output of the particulate matter detection sensor corresponds to the amount of PM.

MODE FOR CARRYING OUT THE INVENTION

First Embodiment

[Configuration of First Embodiment]

Figure 1:
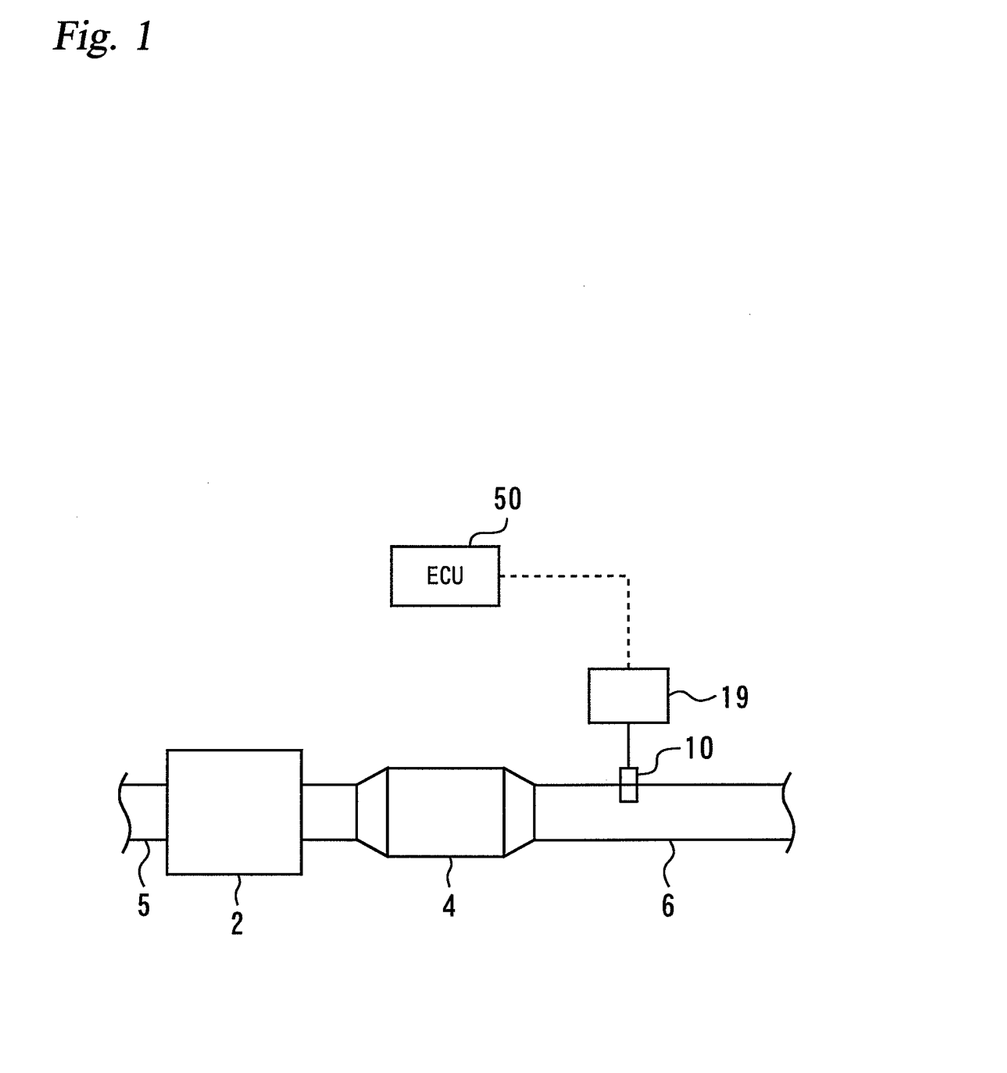
FIG. 1 is a diagram illustrating the configuration of an abnormality determination device according to a first embodiment of the present invention.

FIG. 1 is a diagram illustrating the configuration of an abnormality determination device according to a first embodiment of the present invention, which is used for a particulate matter detection sensor (PM sensor). This figure also shows an internal combustion engine 2 to which the abnormality determination device is applied. The abnormality determination device according to the first embodiment can be suitably used to determine whether or not a PM sensor included in an internal combustion engine for a vehicle or other movable body is abnormal.

The configuration of the internal combustion engine 2 shown in FIG. 1 is not particularly limited. However, the internal combustion engine 2 may include a plurality of cylinders (two or more cylinders, for example, four cylinders or six cylinders) that are arranged in various ways (e.g., in-line or V-type). For example, a four-stroke reciprocating engine may be used as the internal combustion engine 2. In the first embodiment, the internal combustion engine 2 is a diesel engine and a multi-cylinder engine commonly used as a vehicle internal combustion engine. Each cylinder of the internal combustion engine 2 has an intake valve and an exhaust valve. The internal combustion engine 2 includes a valve device that drives the intake valve and exhaust valve. It is also assumed that each cylinder also has a fuel injection valve.

An intake port of the internal combustion engine 2 is in communication with an intake path 5. The intake path 5 is provided as needed, for instance, with various pipes (not shown), such as an intake pipe and an intake manifold, and various intake sensors (not shown), such as an intake pressure sensor, an intake temperature sensor, and an air flow meter. An exhaust port of the internal combustion engine 2, on the other hand, is in communication with a DPF (Diesel Particulate Filter) 4 through an exhaust manifold. The DPF 4 can collect particulate matter (hereinafter may be referred to as the PM) in an exhaust gas (burned gas) discharged from the internal combustion engine 2.

An exhaust pipe 6 is installed downstream of the DPF 4 and in communication with the DPF 4. The exhaust gas passing through the DPF 4 flows into the exhaust pipe 6. A PM sensor 10 is disposed in the exhaust pipe 6. As the PM sensor 10 is positioned downstream of the DPF 4, it can detect the amount of PM in the exhaust gas downstream of the DPF 4. The PM sensor 10 is connected to a control circuit section 19. The control circuit section 19 functions as a so-called controller for the PM sensor 10, connects to an output terminal of the PM sensor 10, receives an electrical signal from the PM sensor 10, and transmits the received electrical signal to an ECU (Electronic Control Unit) 50.

The ECU 50 shown in FIG. 1 functions as a control device for controlling the internal combustion engine 2. An intake system and exhaust system of the internal combustion engine 2 include various sensors (not shown) for controlling the internal combustion engine 2. For example, a crank angle sensor is included to output a signal CA in accordance with the rotation angle of a crankshaft. The signal CA of the crank angle sensor can be used to calculate an engine speed (the number of revolutions per unit time) and an in-cylinder volume, which is determined by the position of a piston. The amount of PM in the exhaust gas varies with operating conditions for the internal combustion engine. The first embodiment utilizes this fact to let the ECU 50 perform an estimation process in which the amount of PM in the exhaust gas is estimated in accordance with the operating conditions (including the outputs of the various sensors) for the internal combustion engine 2. The ECU 50 processes signals from the sensors and reflects the results of such processing in the operations of various actuators (actuators for controlling the internal combustion engine 2). The exhaust system of the internal combustion engine 2 includes a catalyst (not shown) for purifying the exhaust gas. Various exhaust gas sensors (e.g., a sensor for detecting the NOx concentration in the exhaust gas) may be installed as needed.

Figure 2:
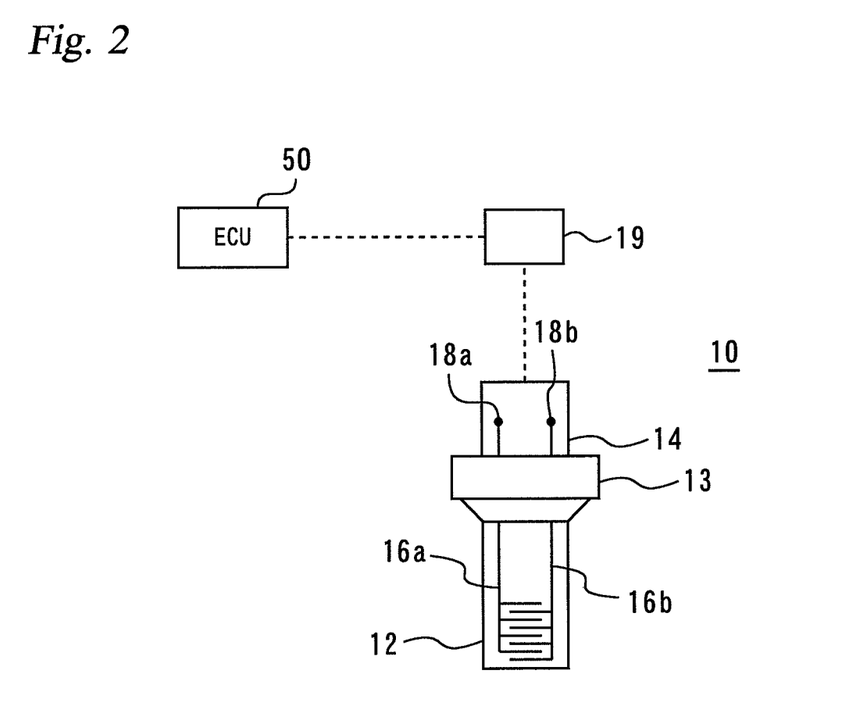
FIG. 2 is an enlarged schematic diagram illustrating a PM sensor according to the first embodiment.

FIG. 2 is an enlarged schematic diagram illustrating the PM sensor 10 according to the first embodiment. This diagram illustrates the configuration of a sensor element section 12 of the PM sensor 10. The PM sensor 10 according to the first embodiment is an electrically resistive PM sensor. The PM sensor 10 includes the sensor element section 12. The sensor element section 12 has a main body that is made, for instance, of alumina and uniform in thickness. Opposing comb-shaped electrodes 16a, 16b made of platinum are formed in the main body as shown, for instance, in FIG. 2. A portion of the sensor element section 12 in which the electrodes 16a, 16b are formed is disposed in an exhaust gas distribution path in which a PM content is detected, and brought into contact with the PM in the exhaust gas.

The PM sensor 10 includes a cover mount 13 and a holding part 14. A covering member (not shown) is installed over the cover mount 13 to surround the sensor element section 12. While the covering member is placed in its position, the sensor element section 12 is exposed to an exhaust gas path, that is, the exhaust pipe 6. When the PM in the exhaust gas enters the covering member and attaches to the electrodes 16 in the sensor element section 12, the electrical resistance between the comb-shaped electrodes 16a, 16b changes. The amount of PM in the exhaust gas can be detected by reading such an electrical resistance change caused by the attached PM from an output signal (output voltage) of the PM sensor 10. In the first embodiment, the PM sensor 10 has such output characteristics that its output voltage V increases with an increase in the amount of PM attached to the sensor element section 12.

The PM sensor 10 includes a heater (not shown), which is mounted on the rear surface of the sensor element section 12 (on the hidden surface of the sensor element section 12 shown in FIG. 2), that is, positioned opposite the electrodes 16a, 16b. In other words, the sensor element section 12 has a certain thickness and two opposing surfaces. The electrodes 16a, 16b are disposed on one of the two opposing surfaces, whereas the heater is disposed on the remaining surface. The heater is connected to the control circuit section 19. The ECU 50 can control the heater through the control circuit section 19. More specifically, the ECU 50 can control the heating temperature of the heater by adjusting the amount of electrical current. The heater is capable of generating heat as needed to heat the sensor element section 12 to a PM elimination temperature, that is, the temperature at which the PM attached to the sensor element section 12 is eliminated. Allowing the heater to heat the sensor element section 12 to the PM elimination temperature makes it possible to eliminate the PM attached to the sensor element section 12 and restore (initialize) the PM detection capability of the sensor element section 12.

The holding part 14 is used to mount the PM sensor 10 on an inner wall of the exhaust pipe 6. More specifically, the holding part 14 has, for instance, a threaded surface for fastening the PM sensor 10 to a mount on the inner wall of the exhaust pipe 6. A wiring section including terminals 18a, 18b is extended into the holding part 14. The terminal 18a is connected to the electrode 16a, whereas the terminal 18b is connected to the electrode 16b. The control circuit section 19 is connected to the terminals 18a, 18b although such connections are briefly shown in FIG. 2, and is capable of receiving voltage changes corresponding to the amount of PM attached to the sensor element section 12 (the amount of PM accumulated on the surface of the sensor element section 12). In accordance with changes in the electrical resistance between the electrodes 16a, 16b, the ECU 50 can detect the amount of attached PM through the control circuit section 19.

In the first embodiment, while the PM sensor is used during an operation of the internal combustion engine 2, a voltage is applied to the electrode section (between the electrodes 16a, 16b). The applied voltage can generate static electricity that promotes PM attachment to the sensor element section 12.

[Operations of First Embodiment]
(Basic Abnormality Determination Operation According to First Embodiment)

When an output change exhibited by the PM sensor 10 is caused normally by the PM, the result of detection based on the output change can be properly used. However, the inventors of the present invention have found, as a result of intensive studies, that changes in the output of the PM sensor 10 may also be brought about by various factors other than the PM in addition to normal output changes. Output changes brought about by factors other than the PM are abnormal output changes and cannot be used as the basis of detecting the existence and amount of PM. The results of detection based on such abnormal output changes cannot be used as the results of PM amount detection or the like. Failure to accurately distinguish between PM sensor output changes caused by factors other than the PM and normal PM sensor output changes may decrease the PM detection accuracy of the PM sensor 10 or cause erroneous PM detection.

In view of the above circumstances, the abnormality determination device according to the first embodiment of the present invention distinguishes between PM sensor output changes caused by factors other than the PM and normal PM sensor output changes caused by the PM by using the method described below.

If an output change exhibited by the PM sensor 10 is caused by the PM attached to the sensor element section 12, the heater heats the sensor element section so that the PM attached to the sensor element section 12 is removed at the PM elimination temperature. This causes the PM sensor 10 to exhibit an output change in accordance with the elimination of the PM. If, on the contrary, an output change caused by the heater's heating operation is encountered at a temperature other than the PM elimination temperature, it is conceivable that the output change exhibited by the PM sensor 10 is not caused by the PM attached to the sensor element section 12. If an expected output change does not occur when the heater performs a heating operation to eliminate the attached PM at the PM elimination temperature, it is conceivable that the output change exhibited by the PM sensor 10 is not caused by the PM attached to the sensor element section 12.

In view of the above circumstances, the first embodiment controls the heater to heat the sensor element section 12, and determines, in accordance with a PM sensor output change caused by such a heater control operation, whether or not the PM sensor 10 is abnormal. When it is necessary to determine whether or not the PM sensor 10 is abnormal, the above-described method according to the first embodiment can distinguish between abnormal output changes in the PM sensor 10 that are caused by factors other than the PM and normal output changes caused by PM. This makes it possible to determine whether PM detection is abnormal.

(Details of Abnormality Determination Method According to First Embodiment)

The abnormality determination device according to the first embodiment will now be described in detail. The following description first deals with a concrete example in which the PM sensor abnormality determination method according to the first embodiment is used, and then deals with a preferred embodiment of the present invention that effectively achieves PM sensor abnormality determination in a situation indicated by the concrete example.

Figure 3:
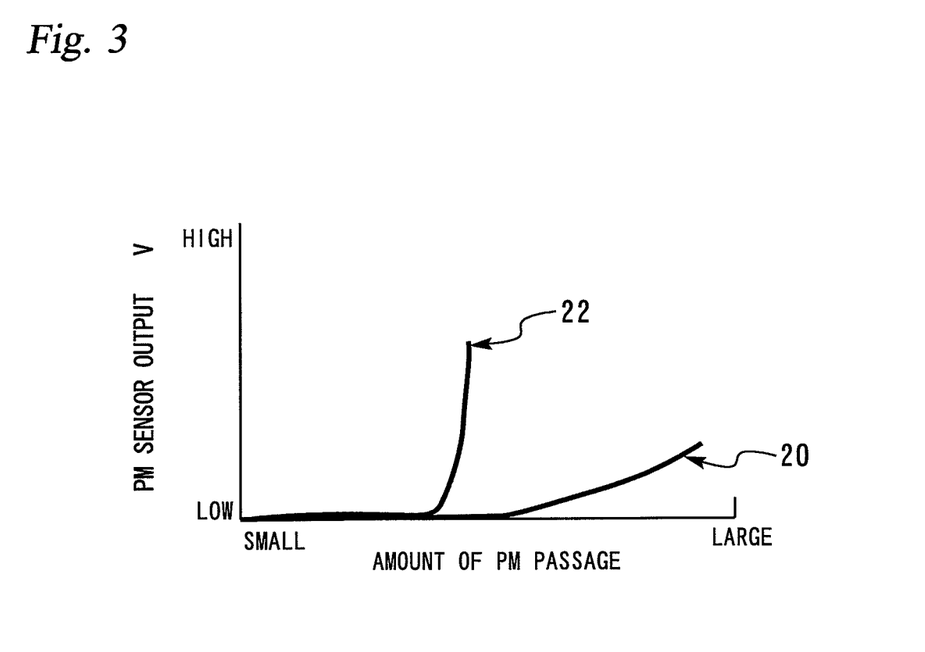
FIG. 3 is a diagram illustrating the relationship between the output voltage V of a PM sensor and the amount of PM passage.

FIG. 3 is a diagram illustrating the relationship between the output voltage V of the PM sensor 10 and the amount of PM passage. The amount of PM passage (mg), which is shown in FIG. 3, correlates with the cumulative amount of PM passage through a position at which the PM sensor 10 is mounted. The amount of PM passage can be obtained, for instance, by determining the estimated amount of PM in accordance with the operating conditions for the internal combustion engine 2. The estimated amount of PM can be determined, for instance, by estimating the amount of discharged PM in accordance with the operating conditions.

In FIG. 3, a curve identified by the reference numeral 20 (hereinafter may be referred to as the "characteristic 20" for the sake of convenience) represents the relationship between the output voltage V and the amount of PM passage that prevails when the PM sensor 10 and the DPF 4 are normal. Even when the DPF 4 is normal (that is, the DPF 4 is not defective), an extremely small amount of PM flows downstream of the DPF 4 so that the PM attaches to (deposits on) the sensor element section 12 little by little. If this condition is allowed to continue for an extended period of time, the amount of attached PM increases to change the electrical resistance between the electrodes 16a, 16b. The output voltage of the PM sensor 10 then changes as indicated by the characteristic 20 shown in FIG. 3. Therefore, if the above condition is allowed to continue for a sufficiently long period of time, the output of the PM sensor 10 changes in accordance with an increase in the amount of attached PM, as indicated by the characteristic 20, even when the DPF 4 collects the PM normally.

On the other hand, a curve identified by the reference numeral 22 in FIG. 3 (hereinafter may be referred to as the "characteristic 22" for the sake of convenience) schematically represents characteristics that prevail when an exhaust gas having a high PM concentration flows to the PM sensor 10 due to a fault in the DPF 4. As compared to the characteristic 20, which represents a normal situation, the characteristic 22 rises sharply. If the output change indicated by the characteristic 22 is caused normally by the PM, the DPF 4 can be determined to be faulty because the amount of PM detected downstream of the DPF 4 is considerably larger than the amount of PM passage through the DPF 4, which is estimated from the operating conditions. However, the PM sensor output change indicated by the characteristic 22 may be caused by various factors other than the PM. In other words, if the PM sensor 10 exhibits a sharp output change indicated by the characteristic 22, it is conceivable that the PM sensor 10 may be in a state different from a normal state (characteristic 20), that is, may be in an abnormal state.

Therefore, the sharp output change indicated by the characteristic 22 should preferably be checked to determine whether it is a normal output change caused by the PM.

The inventors of the present invention have found as a result of intensive studies that, in the first embodiment, a PM sensor output change indicated by the characteristic 22 shown in FIG. 3 may be caused by at least four factors described below:

(A) A sharp increase in the amount of discharged PM due to a fault in the DPF 4

(B) Electrical short-circuiting of the electrode section (electrodes 16a, 16b) of the PM sensor 10

(C) Attachment of a substance other than the PM (such as water, fuel, or organic matter) to the electrode section (electrodes 16a, 16b) of the sensor element section 12

(D) Water condensation on the wiring section (the interior of the holding part 14) of the PM sensor 10

When an output change indicated by the characteristic 22 is caused by factor (A), it can be concluded that the PM detection capability of the PM sensor 10 is normal. If, on the other hand, an output change indicated by the characteristic 22 is caused by factor (B), (C), or (D), the PM detection capability of the PM sensor 10 is not normal so that the output change in the PM sensor 10 is not a normal output change caused by the PM.

In the first embodiment, therefore, the results of analyses conducted by the inventors of the present invention to examine the factors causing output changes are used to check for an abnormality in the PM sensor 10 in accordance with PM sensor output changes caused by later-defined heater temperature control.

Figure 4:
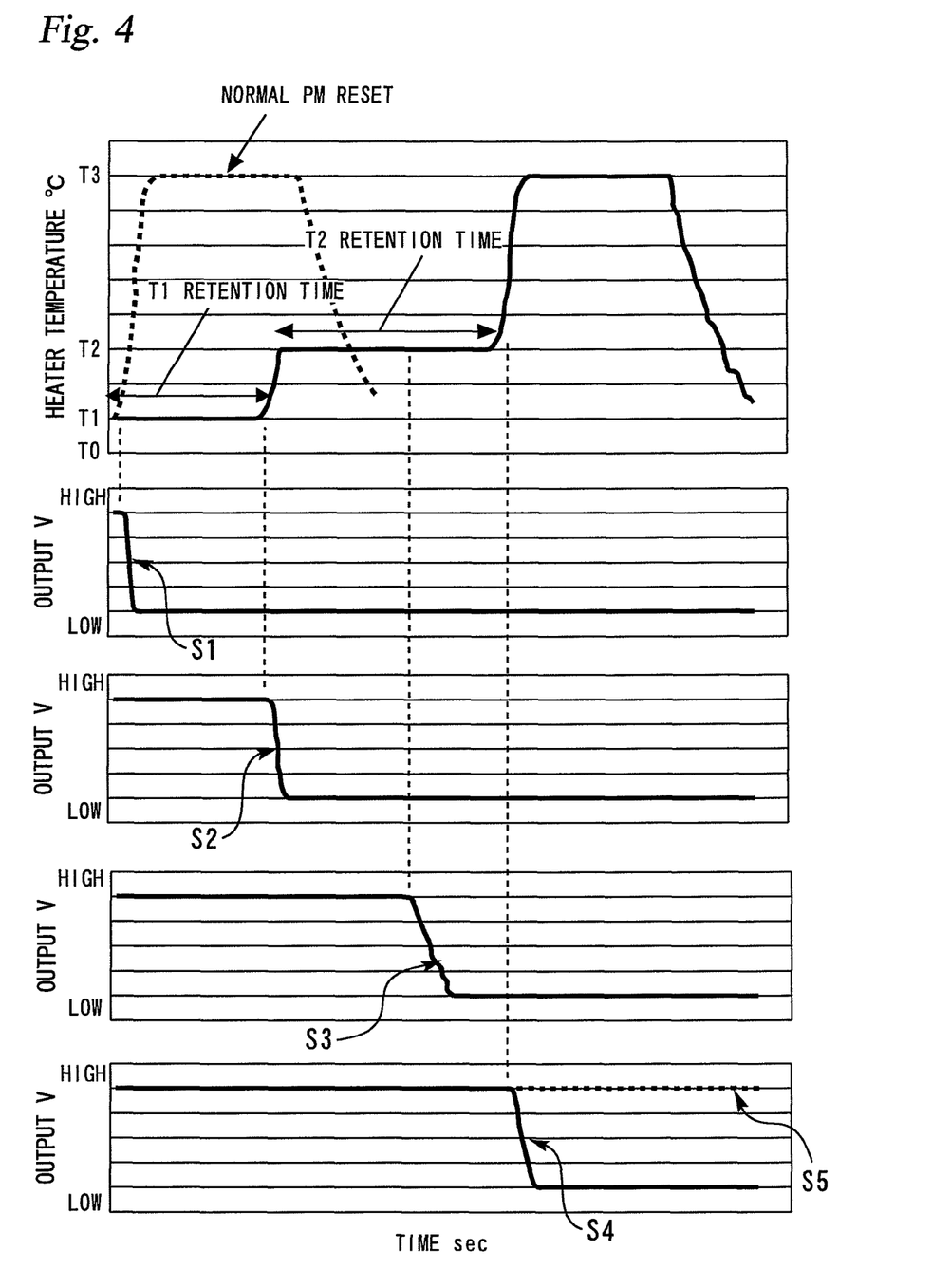
FIG. 4 is a diagram illustrating an operation of the abnormality determination device according to the first embodiment of the present invention.

FIG. 4 is a diagram illustrating an operation of the abnormality determination device according to the first embodiment of the present invention. The uppermost graph in FIG. 4 shows the temperature of the heater (not shown) for the sensor element section 12. In this graph, the heater temperature is indicated along the vertical axis, whereas time is indicated along the horizontal axis (the time progresses in a rightward direction in FIG. 4). The lower graphs show the output voltage of the PM sensor 10. In these graphs, the output voltage value is indicated along the vertical axis, whereas time is indicated along the horizontal axis. The uppermost graph and lower graphs in FIG. 4 use the same scale of horizontal axis (time axis). As described earlier, it is assumed in the first embodiment that the output voltage V of the PM sensor 10 increases with an increase in the amount of PM attached to the sensor element section 12, and that heater temperature control shown in FIG. 4 is initiated when the output voltage V is built up (is high).

A heater temperature characteristic (a "normal PM reset"), which is indicated by a broken line in FIG. 4, represents heater temperature control that is exercised to eliminate the PM from the PM sensor 10 without using the abnormality determination method according to the first embodiment. In the case of the "normal PM reset," the heater temperature immediately rises to T3 upon heater ON so that the sensor element section 12 is heated to the PM elimination temperature. The "normal PM reset" makes it possible to eliminate the PM immediately and restore the PM detection capability of the PM sensor 10 to its initial state.

A heater temperature characteristic indicated by a solid line in FIG. 4 represents heater temperature control that is exercised by using the abnormality determination method according to the first embodiment. The first embodiment differs from the "normal PM reset" in that stepwise (gradual) heater temperature control is exercised as indicated by the solid line in FIG. 4.

FIG. 4 shows the output of the PM sensor 10 and the heater temperature after heater temperature control is initiated in accordance with the first embodiment. In the first embodiment, the PM sensor 10 is not heated by the heater (the heater is turned off by the ECU 50) before the start of heater temperature control shown in FIG. 4. It is therefore assumed that the heater temperature indicated in FIG. 4 is T0, which is lower than T1. In the first embodiment, the temperature of the sensor element section 12 during a period during which the heater is not performing a heating operation is left uncontrolled and affected, for instance, by the temperature of the exhaust gas.

Operations performed for heater temperature control and PM sensor abnormality determination according to the first embodiment will now be described. If there arises a situation where the PM sensor 10 needs to be checked for an abnormality as exemplified in FIG. 3, the following abnormality determination method can be exercised to determine whether or not the PM sensor 10 is abnormal.

(Temperature T1)

First of all, the heater is turned on and controlled to raise its temperature to T1. The temperature T1 is a heater temperature that is high enough to evaporate the "water attached to the sensor element section 12." More specifically, the temperature T1 can be set as appropriate within the range of approximately 150° C. to 200° C.

If an output change indicated by the characteristic 22 is caused by the "water attached to the electrode section of the sensor element section 12" in a situation where the temperature T1 is defined as described above, the water attached to the electrode section is removed as the heater temperature is raised to T1. As the water attached to the electrode section is removed, the output of the PM sensor 10 changes from high to low. As a result, the output of the PM sensor 10 changes as indicated by S1 in FIG. 4 because the heater temperature is raised to T1. Checking whether the output change S1 attributable to the temperature T1 is detected makes it possible to determine whether or not "water is attached to the electrode section," which is a part of the aforementioned factor (C).

In the first embodiment, it is assumed that the heater is maintained at the temperature T1 for a predetermined period of time ("T1 retention time" in FIG. 4). Hence, whether there is the output change S1 can be detected with increased accuracy.

If, on the other hand, the output change S1 is not encountered at the temperature T1, it can be concluded that the output change indicated by the characteristic 22 in FIG. 3 is not caused by the "water attached to the electrode section of the sensor element section 12."

(Temperature T2)

If the output change S1 attributable to the temperature T1 is not encountered, the heater temperature is raised from T1 to T2. The temperature T2 is high enough to evaporate a fuel attached to the sensor element section 12. The temperature T2 is higher than the temperature T1 (T1<T2). More specifically, the temperature T2 can be set, for instance, to approximately 300° C. If the evaporation temperature of the fuel attached to the sensor element section 12 varies to some extent with the fuel used for the internal combustion engine 2, the temperature T2 can alternatively be set as appropriate within the evaporation temperature range of the attached fuel.

If the output change indicated by the characteristic 22 is caused by "fuel or organic matter attached to the electrode section of the sensor element section 12" in a situation where the temperature T2 is set as described above, the fuel or organic matter attached to the electrode section is eliminated as the heater temperature is raised to T2. When the fuel or organic matter is eliminated in the above manner, the output of the PM sensor 10 changes from high to low. As a result, the output of the PM sensor 10 changes as indicated by S2 in FIG. 4 as the heater temperature is raised from T1 to T2. Checking whether the output change S2 attributable to the temperature T2 is detected makes it possible to determine whether or not "fuel or organic matter is attached to the electrode section," which is a part of the aforementioned factor (C).

If, on the other hand, the output change S2 is not encountered when the temperature is raised from T1 to T2, it can be concluded that the output change indicated by the characteristic 22 in FIG. 3 is not caused by the "fuel or organic matter attached to the electrode section of the sensor element section 12."

(T2 Retention Time)

If the output change S2 attributable to the temperature T2 is not encountered, the first embodiment maintains the heater at the temperature T2 for a predetermined period of time ("T2 retention time" in FIG. 4) after heater temperature control has been exercised to raise the temperature to T2. The aforementioned factor (D) implies that the PM sensor 10 exhibits the output change indicated by the characteristic 22 due to the "water condensation on the wiring section (the interior of the holding part 14) of the PM sensor 10." After the heater temperature is raised to T2, the condensed water does not always evaporate at once. In some cases, water gradually evaporates and then the condensed water evaporates after the elapse of a certain period of time to restore the output of the PM sensor 10 to normal (cause the output of the PM sensor 10 to increase from a low level to a high level in the first embodiment). An output change S3 in FIG. 4 represents such a case. In the first embodiment, it is assumed that the output change S3 may not occur until a certain period of time elapses after the heater temperature is raised to T2. Therefore, the first embodiment defines the "T2 retention time" as a "period of time long enough to evaporate the water condensed on the wiring section (the interior of the holding part 14) of the PM sensor 10." This makes it possible to accurately check for a phenomenon caused by the aforementioned factor (D).

If, on the other hand, the output change S3 is not encountered within the period of the T2 retention time, it can be concluded that the output change indicated by the characteristic 22 in FIG. 3 is not caused by the "water condensation on the wiring section (the interior of the holding part 14) of the PM sensor 10."

(Temperature T3)

If the output change S3 is not encountered during the T2 retention time, the first embodiment raises the heater temperature from T2 to T3. In the first embodiment, the temperature T3 is a heater temperature for raising the temperature of the sensor element section 12 to the PM elimination temperature as described earlier. It is the same as a target temperature that is used when "normal PM reset" control is exercised. When the output change indicated by the characteristic 22 is caused by the "PM attached to the sensor element section 12," the PM is eliminated from the electrode section as the heater temperature is raised to T2. Upon PM elimination, the output of the PM sensor 10 changes from high to low. As a result, the output of the PM sensor 10 changes as indicated by S4 in FIG. 4 as the heater temperature is raised from T2 to T3. Checking whether the output change S4 attributable to heater temperature control for raising the temperature from T2 to T3 is detected makes it possible to determine whether or not the PM sensor 10 has normally exhibited an output change caused by the attached PM.

Further, as the obtained result indicates that a change in the output of the PM sensor 10 is normal, it can be concluded that the characteristic 22 is derived from factor (A), that is, "a sharp increase in the amount of discharged PM due to a fault in the DPF 4."

Meanwhile, if, as implied by an output S5, which is indicated by a broken line in FIG. 4, the output voltage of the PM sensor 10 remains high even after heater temperature control has been exercised to raise the temperature to T3, the output of the PM sensor 10 remains unchanged although the PM is eliminated. If such a phenomenon occurs, it is conceivable that there is a hardware fault in the PM sensor 10. In this case, the first embodiment concludes that the encountered phenomenon is caused by the aforementioned factor (B), which is "electrical short-circuiting of the electrode section (electrodes 16a, 16b) of the PM sensor 10."

The temperatures T1, T2, T3 should be defined in accordance with the results of experiments conducted along the above-described principles and in consideration of detailed specifications for individual PM sensor products. Further, the ECU 50 or a heater control circuit, if it is provided, should exercise stepwise heater temperature control as indicated by the uppermost graph in FIG. 4.

[Details of Process Performed by First Embodiment]

Figure 5:
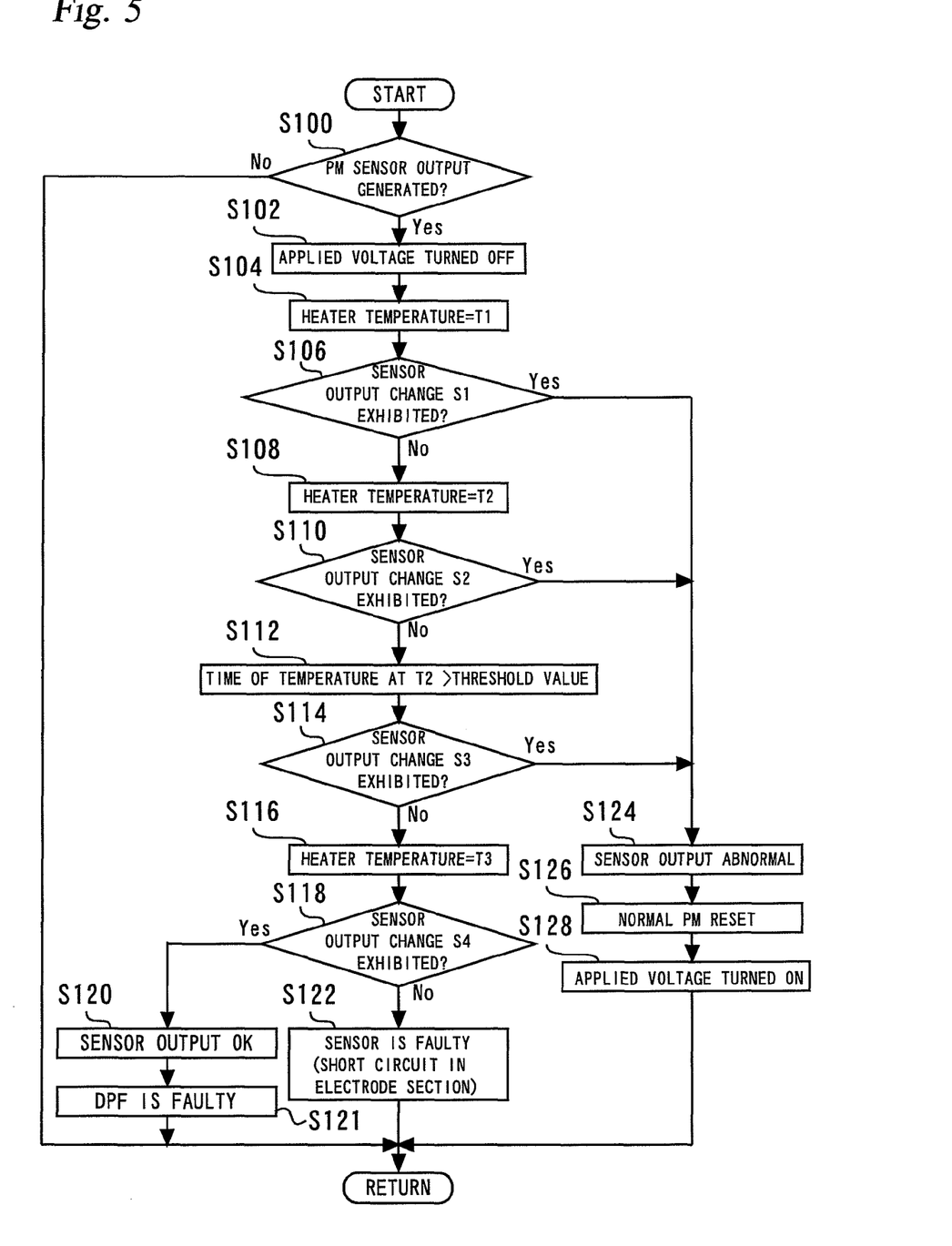
FIG. 5 is a flowchart illustrating a routine that is executed by ECU (Electronic Control Unit) in the first embodiment.

A process performed by the abnormality determination device according to the first embodiment will now be described in detail with reference to FIG. 5. FIG. 5 is a flowchart illustrating a routine that is executed by the ECU 50 in the first embodiment. The routine is executed while the internal combustion engine 2 operates. It is assumed that the routine is repeatedly executed at predetermined time intervals.

The routine shown in FIG. 5 first performs step S100 in which the ECU 50 determines whether a predefined PM sensor output is generated. In step S100, the ECU 50 performs a predetermined determination process to determine whether a sharp output change indicated, for instance, by the aforementioned characteristic 22 in FIG. 3 is encountered. The determination process is performed to determine whether a rate of change in the output voltage of the PM sensor 10 is higher than a predetermined value, that is, the change in the output of the PM sensor 10 is sharper than a change indicated by the predetermined change rate. The output voltage change rate may be a value indicative of "the amount of output voltage change per unit amount of PM passage." The unit amount of PM passage can be obtained by first determining the estimated amount of PM in accordance with the operating conditions for the internal combustion engine 2 as described in connection with FIG. 3 and then calculating the estimated amount of PM passage downstream of the DPF 4 by using the determined estimated amount of PM. The value calculated in this manner can be used as the unit amount of PM passage. A process for estimating the amount of PM can be performed by the ECU 50 separately from the routine shown in FIG. 5. When the output voltage change rate of the PM sensor 10 is evaluated on the basis of the amount of output voltage change per unit amount of PM passage, whether or not the change in the output of the PM sensor 10 is sharp enough to require abnormality determination can be properly determined in various situations where the amount of generated PM varies (i.e., under various operating conditions). An alternative is to determine the amount of output voltage change per unit time instead of the amount of output voltage change per unit amount of PM passage.

If the predefined PM sensor output is not generated in step S100, the routine terminates so that the process returns.

If the determination result obtained in step S100 is affirmative (the query in step S100 is answered "YES"), the ECU 50 proceeds to step S102 and turns off the voltage applied to the PM sensor 10. Upon completion of step S102, the promotion of PM attachment to the sensor element section 12 comes to a stop. In step S102, the output of the PM sensor 10 is "high" to indicate an increase in the amount of attached PM or the detection of a significant amount of PM.

Next, the ECU 50 proceeds to step S104 and exercises control to raise the heater temperature to T1. In step S104, the ECU 50 turns on the heater, which has been off, and adjusts the amount of electrical current supply to the heater as needed to raise the heater temperature to T1.

Next, the ECU 50 proceeds to step S106 and determines whether a predefined output change is exhibited by the PM sensor 10. In step S106, the ECU 50 determines whether the output voltage is decreased as indicated by the aforementioned output change S1 in FIG. 4 in accordance with a heater temperature rise to T1. More specifically, the ECU 50 may, for example, determine whether the output voltage of the PM sensor 10, which was high in step S100, is still high. As described in connection with FIG. 4, it is assumed that the first embodiment certainly checks for the output change S1 by maintaining the temperature T1 for the predetermined T1 retention time.

If the predefined sensor output change is not encountered in step S106 (the query in step S106 is answered "NO"), the ECU 50 proceeds to step S108 and exercises control to raise the heater temperature to T2. In step S108, the ECU 50 adjusts the amount of electrical current supply to the heater as needed to exercise heater temperature rise control so that the temperature rises from T1 to T2 as indicated by the stepwise temperature characteristics shown in FIG. 4.

Next, the ECU 50 proceeds to step S110 and determines whether the predefined sensor output change S2 is exhibited by the PM sensor 10. In step S110, the ECU 50 determines whether the output voltage is decreased as indicated by the aforementioned output change S2 in FIG. 4 in accordance with a heater temperature rise to T2. More specifically, the ECU 50 may, for example, determine whether the output voltage of the PM sensor 10 is still high.

If the predefined sensor output change S2 is not encountered in step S110 (the query in step S110 is answered "NO"), the ECU 50 proceeds to step S112 and maintains the temperature T2 for a predetermined period of time. In step S112, the ECU 50 keeps the heater temperature at T2 and refrains from changing the heater temperature (prevents an increase in the heater temperature) until a predetermined threshold value is exceeded by the elapsed time after temperature control to T2. The process performed in step S112 is a part of an abnormality determination process concerning the aforementioned T2 retention time.

Upon completion of the above step, the ECU 50 proceeds to step S114 and determines again whether the predefined output change S3 is exhibited by the PM sensor 10. In step S114, the ECU 50 determines whether the output voltage is decreased as indicated by the aforementioned output change S3 in FIG. 4 during the T2 retention period during which the temperature T2 is maintained. More specifically, the ECU 50 may, for example, determine whether the output voltage of the PM sensor 10 is still high.

If the predefined sensor output change S3 is not encountered in step S114 (the query in step S114 is answered "NO"), the ECU 50 proceeds to step S116 and exercises control to raise the heater temperature to T3. In step S116, the ECU 50 adjusts the amount of electrical current supply to the heater as needed to exercise heater temperature rise control so that the temperature rises from T2 to T3 as indicated by the stepwise temperature characteristics shown in FIG. 4.

Next, the ECU 50 proceeds to step S118 and determines whether the predefined output change S4 is exhibited by the PM sensor 10. In step S118, the ECU 50 determines whether the output voltage is decreased as indicated by the aforementioned output change S4 in FIG. 4 in accordance with a heater temperature rise to T3. More specifically, the ECU 50 may, for example, determine whether the output voltage of the PM sensor 10 is still high.

If the predefined sensor output change S4 is not encountered in step S118 (the query in step S118 is answered "NO"), the ECU 50 proceeds to step S122 and outputs an abnormality determination result to indicate that the sensor is faulty (there is a short circuit in the electrode section). If the heater heats the sensor element section 12 to the PM elimination temperature after an output change equivalent to an increase in the amount of attached PM is exhibited by the PM sensor 10 (after an output is generated in step S100), the PM should be eliminated from the sensor element section 12 so that the PM sensor 10 exhibits the output change S4 equivalent to a decrease in the amount of attached PM. However, if, contrary to the above expectation, the PM sensor 10 does not exhibit the output change S4, it is conceivable that the output change equivalent to an increase in the amount of attached PM is caused by a factor other than the attached PM. When the above is taken into consideration, the first embodiment can accurately distinguish between the PM sensor's normal output changes caused by the PM and output changes caused by factors other than the PM (more specifically, the first embodiment assumes that there is a short circuit in the electrode section). Subsequently, the routine terminates so that the process returns.

If, on the contrary, the predefined sensor output change S4 is encountered in step S118 (the query in step S118 is answered "YES"), the ECU 50 proceeds to step S120 and outputs a determination result to indicate that the sensor output is normal. Thus, the obtained determination result indicates that the PM sensor 10 is normal. If the PM attached to the PM sensor 10 needs to be eliminated after the above determination result is obtained, the aforementioned "normal PM reset" may be performed.

Next, the ECU 50 further proceeds to step S121 and outputs a determination result to indicate that the DPF 4 is faulty. In the first step (step S100) of the routine shown in FIG. 5, the ECU 50 performs the predetermined determination process to determine whether a sharp output change indicated, for instance, by the aforementioned characteristic 22 in FIG. 3 is encountered. If the PM sensor 10 is normal, it can be concluded that the sharp output change encountered in step S100 is caused by "a sharp increase in the amount of discharged PM due to a fault in the DPF 4." As the first embodiment can output a determination result in step S121 to indicate that there is a fault in the DPF 4, it is possible to immediately cope with the fault in the DPF 4. Subsequently, the routine terminates so that the process returns.

If, on the other hand, a sensor output change is encountered in step S106, S110, or S114 (the query in step S106, S110, or S114 is answered "YES"), the ECU 50 proceeds to step S124 and outputs a determination result to indicate that the sensor output is abnormal. In step S124, the ECU 50 can output a determination result to indicate that the PM sensor output generated in step S100 is abnormal.

Next, the ECU 50 proceeds to step S126 and executes a process for performing the "normal PM reset." In step S126, the ECU 50 sets the heater temperature to T3 and allows the sensor element section 12 to be immediately heated in accordance with the heater temperature characteristic ("normal PM reset"), which is indicated by a broken line in FIG. 4. The substance attached to the PM sensor 10, including the PM, is then eliminated so that the PM detection capability of the PM sensor 10 can be restored.

Upon completion of step S126, the ECU 50 proceeds to step S128 and turns on the applied voltage, which was turned off in step S102. Subsequently, the routine terminates so that the process returns.

Performing the above-described process makes it possible to determine, in accordance with PM sensor output changes brought about by heater control, whether or not the PM sensor 10 is abnormal. If it is necessary to check for an abnormality in the PM sensor 10 due to a sharp output change indicated, for instance, by the characteristic 22 in FIG. 3, it is possible to check for the PM sensor's abnormal PM detection by distinguishing between the PM sensor's normal output changes caused by the PM and abnormal output changes caused by factors other than the PM.

In the abnormality determination device according to the first embodiment, the ECU 50 can perform a heater control process to heat the sensor element section 12 after the PM sensor 10 exhibits an output change equivalent to an increase in the amount of PM attached to the sensor element section 12 (or the electrode section). Further, the ECU 50 can check whether output changes (S1, S2, S3) equivalent to a decrease in the amount of PM attached to the sensor element section 12 are encountered while the temperature of the sensor element section 12 is lower than the PM elimination temperature T3 (is equal to or higher than T0 and lower than T3) due to heater control exercised to heat the sensor element section 12. As a result of this check, the ECU 50 can determine whether or not the PM sensor 10 is abnormal. If an output change equivalent to a decrease in the amount of attached PM is encountered due to heating by the heater, although the temperature is lower than the PM elimination temperature, after an output change equivalent to an increase in the amount of attached PM is exhibited by the PM sensor 10, it is conceivable that the output change equivalent to an increase in the amount of attached PM is caused by a factor other than the attached PM. When this is taken into consideration, it is possible to accurately distinguish between the PM sensor's normal output changes caused by the PM and output changes caused by factors other than the PM.

In the first embodiment described above, the PM sensor 10 corresponds to the "particulate matter detection sensor" according to the first aspect of the present invention; the sensor element section 12 corresponds to the "sensor element section" according to the first aspect of the present invention; the wiring section (including the terminals 18a, 18b) and the control circuit section 19 correspond to the "output means" according to the first aspect of the present invention; and the heater (not shown) on the back surface of the sensor element section 12 corresponds to the "heater" according to the first aspect of the present invention.

Further, in the first embodiment described above, the "heater control means" according to the first aspect of the present invention is implemented when the ECU 50 performs steps S104, S108, S112, and S116 of the routine shown in FIG. 5; and the "determination means" according to the first aspect of the present invention is implemented when the ECU 50 performs steps S106, S110, S114, S118, S120, and S124.

Furthermore, in the first embodiment described above, the "specific-temperature heater control means" according to the third aspect of the present invention is implemented when the ECU 50 exercises heater temperature control in steps S104 and S106 of the routine shown in FIG. 5 or when the ECU 50 exercises heater temperature control in steps S108, S110, and S112.

Moreover, in the first embodiment described above, three-step temperature control is exercised to raise the temperature from T0 through T1 and T2 to T3 as shown in FIG. 4 when the ECU 50 performs steps S104, S108, S112, and S116. The "stepwise heater control means" according to the fourth aspect of the present invention is implemented by the above-mentioned three-step temperature control.

In addition, in the first embodiment described above, the "first control" according to the fifth aspect of the present invention is implemented when the ECU 50 exercises heater temperature control in steps S104 and S106 of the routine shown in FIG. 5; and the "second control" according to the fifth aspect of the present invention is implemented when the ECU 50 exercises heater temperature control in steps S108, S110, and S112.

In the first embodiment described above, the output changes S1, S2, S3 in the PM sensor 10 correspond to the "first output change" according to the sixth aspect of the present invention; and the output change S4 in the PM sensor 10 corresponds to the "second output change" according to the sixth aspect of the present invention.

Further, in the first embodiment described above, the PM sensor 10 corresponds to the "PM sensor" according to the ninth aspect of the present invention; the sensor element section 12 corresponds to the "sensor element section" according to the ninth aspect of the present invention; the holding part 14 corresponds to the "holding part" according to the ninth aspect of the present invention; and the wiring section including the terminals 18a, 18b corresponds to the "wiring section" according to the ninth aspect of the present invention.

Furthermore, in the first embodiment described above, the "determination start means" according to the twelfth aspect of the present invention is implemented when the ECU 50 performs step S100.

Moreover, in the first embodiment described above, the DPF 4 corresponds to the "particulate filter" according to the thirteenth aspect of the present invention; the PM sensor 10 corresponds to the "PM sensor" according to the thirteenth aspect of the present invention; and the "fault determination means" of the "fault determination device for a particulate matter collection system" according to the thirteenth aspect of the present invention is implemented when the ECU 50 performs step S121 of the routine shown in FIG. 5.

[Example Modifications of First Embodiment]

In the hardware configuration according to the first embodiment, an electrically resistive PM sensor 10 is used as particulate matter detection sensor. In accordance with the magnitude of an output voltage, the PM sensor 10 can indicate the amount of attached PM and the attachment of a significant amount of PM. However, the present invention is not limited to such a PM sensor. Various other PM sensors may also be used as far as they are capable of changing their output (output voltage, output current, or other output signal) in accordance with attached PM and eliminating the attached PM with a heater. For example, a capacitance PM sensor may be used instead of an electrically resistive PM sensor. Further, the PM sensor used in the first embodiment changes its output voltage from low to high in accordance with an increase in the amount of attached PM. However, the present invention is not limited to such a PM sensor. Due, for instance, to circuit configuration differences between individual sensors, the first embodiment may use a PM sensor whose output voltage conversely changes from high to low in accordance with an increase in the amount of attached PM. The present invention is also applicable to such a PM sensor as far as output changes brought about by heater temperature control are checked for.

In the first embodiment, three-step heater temperature control is exercised to raise the temperature from T0 through T1 and T2 to T3. However, the present invention is not limited to such heater temperature control. Heater temperature control may alternatively be provided in two steps or four or more steps. For example, heater temperature control need not always be provided in all three steps. One of the three steps may be omitted. More specifically, heater temperature control may be exercised, for instance, to merely raise the temperature to T1 and check for the output change S1. Alternatively, heater temperature control may be exercised to merely raise the temperature to T2 and check for the output change S2. Further, the T2 retention time may be omitted. This omission makes it possible to prevent the detection of a fault in the DPF 4 from being delayed due to a time-consuming abnormality determination process for the PM sensor 10. Another alternative is to exercise heater temperature control for the purpose of merely raising the temperature to T3 and checking whether the output change S4 occurs normally upon PM elimination.

Further, the present invention is not limited to an embodiment in which a temperature rise sequence and a temperature retention sequence alternate as shown in FIG. 4. The present invention is not limited to a case where a controlling value (the amount of electrical current supply) is fixed after a target heater temperature (the amount of electrical current supply to the heater) is reached. Alternatively, control may be exercised in temperature zones between T0 and T1, between T1 and T2, and between T2 and T3 to increase or decrease the temperature (target temperature) in a linear or curved manner at a moderate temperature change rate. In such an instance, the temperature change rates in the individual temperature zones (e.g., the temperature zones between T1 and T2 and between T2 and T3) may remain equal or differ from each other.

Furthermore, in the first embodiment, heater temperature control is exercised to attain target temperatures of T1, T2, and T3 by adjusting the amount of electrical current supply to the heater. However, the present invention is not limited to such a heater temperature control method. For example, heater temperature control may alternatively be exercised to adjust the amount of electrical current supply to the heater in such a manner that the heater temperature is controlled within "a temperature range that is equal to or higher than a temperature at which the output change S1 causes and is lower than a temperature at which the output change S2 causes" or "a temperature range that is equal to or higher than a temperature at which the output change S2 and is lower than a temperature at which the output change S4."

Moreover, heater temperature control according to the present invention is not limited to the stepwise temperature rise control according to the first embodiment, which is shown in FIG. 4. Any heater temperature control may be exercised as far as the output change S4 caused by PM elimination can be distinguished from the output changes S1, S2 caused by the elimination of "an attached substance other than the PM from the sensor element section 12" and the output change S3 caused by the elimination of "water condensed on the wiring section in the holding part 14." Therefore, the amount of electrical current supply to the heater may be increased and adjusted to raise the heater temperature at a temperature rise rate at which the output changes S1, S2, S3 in the PM sensor 10, which occur before the sensor element section 12 reaches the temperature T3, can be distinguished from a PM sensor output change that occurs when the PM is eliminated at the temperature T3. In this instance, the heater temperature characteristic need not always be clearly stepwise as shown in FIG. 4.

In the routine shown in FIG. 5, the ECU 50 outputs a determination result in step S124 to indicate that the sensor output is abnormal. However, the ECU 50 may alternatively output a determination result in step S124 to not only report an abnormal sensor output but also "identify an abnormality in the PM sensor 10." In other words, step S124 may be performed to output a determination result to generate "information indicative of the type of the abnormality in the PM sensor 10" depending on whether an output change is encountered in a determination process performed in step S106, S108, or S114.

If the query in step S106 is answered "YES" (the determination result obtained in step S106 is affirmative), the output change S1 is encountered. If the query in step S110 is answered "YES," the output change S2 is encountered. If the query in step S114 is answered "YES," the output change S3 is encountered. As already explained with reference to FIG. 4, the cause of an abnormality in the PM sensor 10 can be identified as factor (C) or factor (D) in accordance with the encountered output change (S1, S2, or S3). In step S124, therefore, the ECU 50 may output a determination result to indicate that the abnormality is attributable to "water attached to the electrode section of the sensor element section 12" when the query in step S106 is answered "YES" (the output change S1 is detected), indicate that the abnormality is attributable to "fuel or organic matter attached to the electrode section of the sensor element section 12" when the query in step S110 is answered "YES" (the output change S2 is detected), and indicate that the abnormality is attributable to "water condensed on the wiring section (in the holding part 14) of the PM sensor 10" when the query in step S114 is answered "YES" (the output change S3 is detected). This makes it possible to accurately distinguish between an abnormal PM sensor output change and a normal PM sensor output change and identify the type of the encountered abnormality.

In the first embodiment described above, the present invention is applied to the particulate matter collection system in which the PM sensor 10 is installed downstream of the DPF 4 to detect PM downstream of the DPF 4. The system according to the first embodiment uses the PM sensor 10 to detect a fault in the DPF 4 and uses an estimated value based on the operating conditions for the internal combustion engine 2 in order to detect the amount of PM in the exhaust gas. However, the present invention is not limited to such an application.

In a conventionally known system, a PM sensor is installed between the exhaust port of the internal combustion engine 2 and the DPF 4 (that is, installed upstream of the DPF 4) so that the system detects the amount of PM in the exhaust gas in accordance with a value detected by the PM sensor. The abnormality determination device for particulate matter detection sensor according to the present invention can be applied to the above system.

More specifically, in the presently described example modification, the routine shown in FIG. 5 is executed in the hardware configuration shown, for instance, in FIG. 1 to determine whether a normal output change is exhibited by the PM sensor installed between the internal combustion engine 2 and the DPF 4. The installed PM sensor should change its output in accordance with the amount of attached PM and may be of the same electrically resistive type as the PM sensor 10. In the presently described example modification, the exhaust pipe 6 corresponds to the "exhaust gas distribution path in which a PM content is detected" according to the fourteenth aspect of the present invention; and the PM sensor 10 corresponds to the "PM sensor" according to the fourteenth aspect of the present invention. If the sensor output is determined to be normal (step S120) in this situation, the amount of PM is detected (by performing, for instance, a calculation process) in accordance with an output value of the PM sensor. If, on the other hand, the sensor output is determined to be abnormal (step S124), the use of the output value of the PM sensor is prohibited. In the presently described example modification, step S121 is excluded from the routine shown in FIG. 5. This implements the "output determination means" and "PM amount detection means" according to the fourteenth aspect of the present invention.

REFERENCE SIGNS LIST

2 internal combustion engine
4 DPF (Diesel Particulate Filter)
5 intake path
6 exhaust pipe
10 PM sensor
12 sensor element section
13 cover mount
14 holding part
16a, 16b electrodes
18a terminal
18a wiring section
18b terminal
19 control circuit section

The invention claimed is:

1. A device for detecting particulate matter in exhaust gas, the device comprising:
   a particulate matter detection sensor that includes a sensor element section installed in an exhaust path of an internal combustion engine, output means for changing an output in accordance with the amount of PM attached to the sensor element section, and a heater capable of heating the sensor element section to a PM elimination temperature at which the PM attached to the sensor element section is eliminated from the sensor element section; and
   a controller configured to acquire the output from the output means, the controller programmed to:
   store a predetermined temperature range, the predetermined temperature range being equal to or higher than a first temperature at which water attached to the sensor element section is eliminated, the predetermined temperature range being lower than a second temperature at which organic matter attached to the sensor element section is eliminated,
   control the heater to heat the sensor element section so that a temperature of the sensor element section becomes within the predetermined temperature range, and
   determine that, when a change in the output of the particulate matter detection sensor in response to the control of the heater is detected in the predetermined temperature range, the particulate matter detection sensor is abnormal.

2. The device according to claim 1, wherein the predetermined temperature range is from 150° C. to 200° C.

3. A device for detecting particulate matter in exhaust gas, the device comprising:
- a particulate matter detection sensor that includes a sensor element section installed in an exhaust path of an internal combustion engine, output means for changing an output in accordance with the amount of PM attached to the sensor element section, and a heater capable of heating the sensor element section to a PM elimination temperature at which the PM attached to the sensor element section is eliminated from the sensor element section; and
- a controller configured to acquire the output from the output means, the controller programmed to:
- store a predetermined temperature range, the predetermined temperature range being equal to or higher than a temperature at which fuel matter attached to the sensor element section or organic matter attached to the sensor element section is eliminated, the predetermined temperature range being lower than the PM elimination temperature,
- control the heater to heat the sensor element section so that a temperature of the sensor element section becomes within the predetermined temperature range, and
- determine that, when an output change in the particulate matter detection sensor in response to the control of the heater is detected in the predetermined temperature range, the particulate matter detection sensor is abnormal.

4. The device according to claim 3, wherein the predetermined temperature range is equal to or higher than 300° C.

5. A device for detecting particulate matter in exhaust gas, the device comprising:
- a particulate matter detection sensor that includes a sensor element section installed in an exhaust path of an internal combustion engine, output means for changing an output in accordance with the amount of PM attached to the sensor element section, and a heater capable of heating the sensor element section to a PM elimination temperature at which the PM attached to the sensor element section is eliminated from the sensor element section; and
- a controller configured to acquire the output from the output means, the controller programmed to:
- store a predetermined first temperature range and a predetermined second temperature range, the predetermined second temperature range being higher than the predetermined first temperature range, the predetermined first temperature range and the predetermined second temperature range being lower than the PM elimination temperature,
- control the heater to heat the sensor element section so that a temperature of the sensor element section becomes within the predetermined first temperature range,
- determine that, when a first output change in the particulate matter detection sensor in response to the heater control is detected in the predetermined first temperature range, the particulate matter detection sensor is in a first abnormal state,
- control the heater to heat the sensor element section after the heater control to the predetermined first temperature range so that the temperature of the sensor element section becomes within the predetermined second temperature range,
- determine that, when a second output change in the particulate matter detection sensor in response to the heater control is detected in the predetermined second temperature range, the particulate matter detection sensor is in a second abnormal state different from the first abnormal state.

6. The device according to claim 5, wherein the predetermined first temperature range is equal to or higher than a temperature at which water attached to the sensor element section is eliminated, the predetermined first temperature range is lower than a second temperature at which organic matter attached to the sensor element section is eliminated, and
- the controller is programmed to determine that the first abnormal state is caused by water attached to the sensor element section.

7. The device according to claim 5, wherein the predetermined first temperature range is 150° C. to 200° C.

8. The device according to claim 5, wherein the predetermined second temperature range is equal to or higher than a temperature at which fuel matter attached to the sensor element section or organic matter attached to the sensor element section is eliminated, the predetermined second temperature range is lower than the PM elimination temperature, and
- the controller is programmed to determine that the second abnormal state is caused by the fuel or the organic matter attached to the sensor element section.

9. The device according to claim 5, wherein the predetermined second temperature range is 300° C. to the PM elimination temperature.

10. The device according to claim 5, wherein
the particulate matter detection sensor further includes:
- a holding part, which is connected to an exhaust pipe of an internal combustion engine and secures the sensor element section to the inside of the exhaust pipe, and
- a wiring section, which is disposed in the holding part and includes wiring for transmitting a signal of the sensor element section to the outside, and wherein the controller is further programmed to:
- control the temperature of the heater in such a manner that the sensor element section is maintained, for a predetermined period of time, within the predetermined second temperature range,
- determine that, when an output change in the particulate matter detection sensor is detected after the heater control to the predetermined second temperature range is started and before a detection time period shorter than the predetermined time period elapses, the particulate matter detection sensor is in the second abnormal state, and
- determine that, when an output change in the particulate matter detection sensor is detected after the detection time period elapses and before the predetermined time period elapses, the particulate matter detection sensor is in a third abnormal state which is different from the first abnormal state and the second abnormal state.

11. The device according to claim 5, wherein
the controller is further programmed to:
- control the heater so that the temperature of the sensor element section becomes within a third temperature range, the third temperature range being equal to or higher than the PM elimination temperature,
- determine that, when a third output change in the particulate matter detection sensor is detected in the third temperature range, the particulate matter sensor is in a normal state.

12. The device according to claim 5, wherein
the particulate matter detection sensor is provided downstream of a particulate filter, the particulate filter is provided in the exhaust channel of an internal combustion engine,
the controller is further programmed to:
control the heater so that the temperature of the sensor element section becomes within a third temperature range, the third temperature range being equal to or higher than the PM elimination temperature,
determine that, when a third output change in the particulate matter detection sensor is detected in the third temperature range, the particulate matter sensor is in a normal state,
determine whether or not the particulate matter detection sensor exhibits a sharp output change sharper than indicated by a predetermined change rate,
execute, when the sharp output change is detected, processings of the heater control to the first temperature range, the determination of the first abnormal state, the heater control to the second temperature range, the determination of the second abnormal state, the heater control to the third temperature range, and the determination of the normal state, in the recited order,
determine that, when the first output change and the second output change are not detected and the third output is detected, the particulate filter is abnormal.

13. The device according to claim 5, wherein
the controller is further programmed to:
execute, when the particulate matter detection sensor exhibits an output change indicating a PM amount increase, processings of the heater control to the first temperature range, the determination of the first abnormal state, the heater control to the second temperature range, the determination of the second abnormal state, in the recited order,
detect the amount of PM based on the output change indicating the PM amount increase when both of the first abnormal state and the second abnormal state are not detected,
not detect the amount of PM based on the output change indicating the PM amount increase when at least one of the first abnormal state and the second abnormal state is detected.

\* \* \* \* \*